United States Patent
Antal et al.

(10) Patent No.: US 6,756,000 B2
(45) Date of Patent: Jun. 29, 2004

(54) PROCESS OF MAKING MULTIFILAMENT YARN

(75) Inventors: Attila Antal, Trenton, NJ (US); Gaoyuan G. Chen, Belle Mead, NJ (US); Dominick Egidio, Flanders, NJ (US); Anthony Tiano, Whiting, NJ (US); Edward Walker, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 367 days.

(21) Appl. No.: 09/969,275

(22) Filed: Oct. 2, 2001

(65) Prior Publication Data

US 2002/0077448 A1 Jun. 20, 2002

Related U.S. Application Data

(60) Provisional application No. 60/237,441, filed on Oct. 3, 2000.

(51) Int. Cl.$^7$ .............................. D01D 5/08; D01D 5/16; D01D 10/02; D01F 6/76; D02G 3/02
(52) U.S. Cl. ................. 264/103; 264/210.7; 264/210.8; 264/235.6
(58) Field of Search ............................... 264/103, 210.7, 264/210.8, 235.6

(56) References Cited

U.S. PATENT DOCUMENTS

| | | |
|---|---|---|
| 4,003,974 A | 1/1977 | Chantry et al. |
| 4,195,052 A | 3/1980 | Davis et al. |
| 4,251,481 A | 2/1981 | Hamlyn |
| 5,102,419 A | 4/1992 | Gertzman et al. |
| 5,232,648 A | 8/1993 | Kennedy et al. |
| 5,288,516 A | 2/1994 | Anderson et al. |
| 5,425,987 A | 6/1995 | Shawver et al. |
| 5,585,056 A | 12/1996 | Liu |
| 5,688,451 A | 11/1997 | Hutton |
| 6,005,019 A | 12/1999 | Liu |

FOREIGN PATENT DOCUMENTS

| | | |
|---|---|---|
| EP | 0 241 252 A2 | 10/1987 |
| EP | 0 415 783 A2 | 3/1991 |
| EP | 1 038 540 A2 | 9/2000 |
| GB | 1 123 445 A | 8/1968 |
| GB | 1 604 177 A | 12/1981 |

OTHER PUBLICATIONS

European Search Report for European Patent Application No. 01308405.8 dated Mar. 28, 2002.

*Primary Examiner*—Leo B. Tentoni

(57) ABSTRACT

The present invention is directed to processes for the manufacture of multifilament yarn, including the steps of extruding multifilaments of a polymer containing at least mole 85 percent L-lactide and not more than 15 mole percent glycolide, spinning the extruded multifilaments to form a spun yarn, passing the spun multifilament yarn through an orientation roll heated at a temperature of less than 98° C. and drawing the spun multifilament yarn to a draw ratio of at least 4:1 to form an oriented multifilament fiber, annealing the oriented multifilament yarn at a temperature greater than that of the orientation roll, and redrawing the annealed, oriented multifilament yarn by at least 10 percent at a temperature lower than the temperature of annealing.

10 Claims, 1 Drawing Sheet

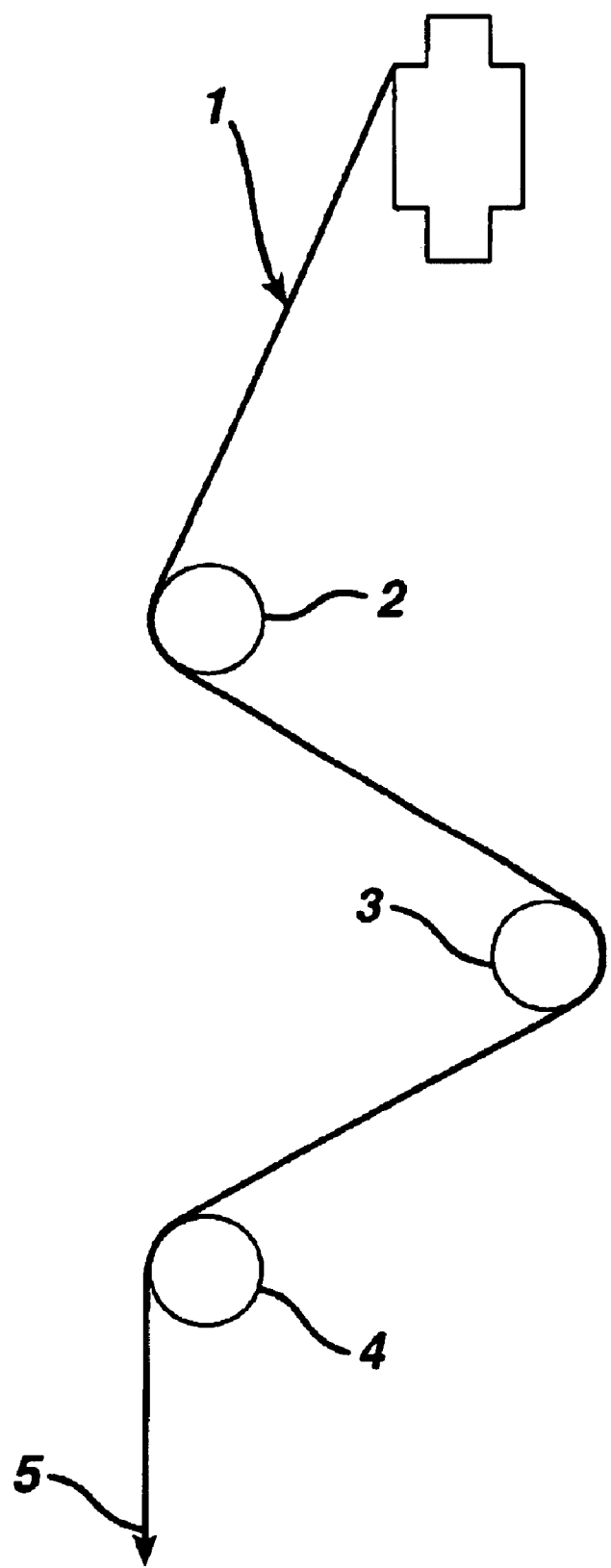

PROCESS OF MAKING MULTIFILAMENT YARN

This application claims the benefit of U.S. Provisional Application No. 60/237,441 filed on Oct. 3, 2000.

FIELD OF THE INVENTION

The present invention relates to processes of making multifilament yarns having properties sufficient for use in medical devices, multifilament yarns prepared by the processes, and medical devices prepared from such multifilament yarns.

BACKGROUND OF THE INVENTION

Medical devices prepared from multifilament yarns made by extruding polymers containing relatively high levels of L-lactide, e.g. greater than about 80 mole percent, and relatively low levels of glycolide, e.g. less than about 20 mole percent, can retain a majority of their original strength after a 6-month in vivo test. Such polymers have relatively slow rates of crystallization and it is very difficult, using known technology for manufacturing such yarns, to form multifilament yarns prepared from such polymers that possess tensile properties effective for use in manufacturing medical devices, e.g. sutures and surgical meshes.

Conventional processes for the formation of high strength multifilament yarns normally include pre-heating extruded, spun multifilament yarn with a known heating means, such as a hot roll, heated pin or the like, drawing the multifilament yarn in one or more drawing steps, and then immediately annealing the drawn yarn with one or more hot annealing rolls in order to "set", or lock-in, the stretched, i.e. drawn, molecular chains. Once the drawn yarns are annealed, they usually are relaxed slightly to reduce the residual internal stress and/or shrinkage before being cooled and wound onto a bobbin. Such processes are described in, e.g. U.S. Pat. No. 4,003,974, the contents of which is incorporated herein by reference in its entirety.

When such conventional processes were used to prepare multifilament yarns prepared from a polymer comprising relatively high L-lactide levels, e.g. about 95 mole percent, it was discovered that the tenacity and strength required for use in the manufacture of medical devices, e.g. sutures, could not be achieved. For example, when such multifilament yarn was drawn with a conventional 1-stage drawing frame, the process resulted in fibers with undesirable tensile properties, such as low tenacity. Over-drawing of the fibers also led to the formation of excessive broken filaments and thus was not effective in improving the yarn tenacity. The drawn yarn average tenacity of yarns prepared according to such conventional processes could barely meet the minimum requirement of 5.6 g/d required for use in absorbable surgical suture products. Traditional process control methods used to optimize the extrusion conditions also was unsuccessful in consistently providing properties required for use in such medical devices.

It would be advantageous to provide processes utilizing more than one drawing step for making multifilament yarns, such that the yarns exhibit properties useful for use in medical devices, e.g. sutures.

SUMMARY OF THE INVENTION

The present invention is directed to processes for the manufacture of multifilament yarn, comprising the steps of extruding and spinning multifilaments of a polymer comprising at least 85 mole percent L-Lactide and not more than 15 mole percent glycolide to form a spun multifilament yarn, passing the spun multifilament yarn through an orientation roll heated at a temperature of less than 98° C. and drawing the spun multifilament yarn to a draw ratio of at least 4:1 to form an oriented multifilament yarn, annealing the oriented multifilament yarn by passing the oriented multifilament yarn over an annealing roll at a minimum temperature that is greater than that of the orientation roll and a maximum temperature that is effective to provide finished multifilament yarn having a tenacity of at least 5.6 grams/denier (g/d); and redrawing the annealed, oriented multifilament yarn by at least 10 percent at a temperature lower than the temperature of the annealing roll. Such processes allow the use of relatively simple equipment to make such yarns, while at the same time providing process stability and good product yield. Multifilament yarns manufactured by the processes of the present invention possess significantly higher strength, greater elongation and toughness, when compared to multifilament yarns prepared by conventional processes. Such multifilament yarns are useful as medical devices, e.g. sutures.

BRIEF DESCRIPTION OF THE DRAWINGS

FIG. 1 is a schematic of apparatus used in the process of the present invention.

DETAILED DESCRIPTION OF THE INVENTION

Advantages of the present invention include unique product properties, e.g. high yarn strength, long term absorbable sutures, less product defects, higher product yield and simplification of processes utilizing two drawing stages. Another advantage of processes according to the present invention is that a conventional one-stage drawing frame may be utilized in yarn manufacturing processes requiring multiple, e.g. two, drawing steps, thus simplifying the equipment used to prepare the yarn and reducing capital and production cost.

Referring to FIG. 1, in one embodiment of the invention a process for forming high strength, absorbable, biocompatible multifilament yarn, comprises the steps of a) extruding via an extruder (not shown) multifilaments of a bioabsorbable polymer melt comprising at least about 85 mole % L-Lactide and not more than about 15 mole percent glycolide, e.g. 95% of L-Lactide and 5% glycolide, and spinning the multifilaments to form spun multifilament yarn 1, b) passing the spun yarn through orientation roll 2 heated at a relatively low temperature, e.g. 80–97° C., and drawing the spun yarn to a draw ratio of at least 4:1 to form an oriented multifilament yarn, c) annealing the oriented multifilament yarn with annealing roll 3 at a temperature higher than the orientation temperature, d) redrawing the annealed filaments by at least 10% with let-off roll 4, which is maintained at ambient temperatures, or a temperature significantly lower than the annealing temperature, and f) winding the yarn with a take-up device (not shown).

The minimum temperature of the annealing roll must be greater than that of the orientation roll. Preferably, the minimum temperature of the annealing roll will be from about 135° C. to about 140° C. The maximum temperature of the annealing roll must be effective to provide finished multifilament yarn having a tenacity of at least 5.6 g/d. By finished multifilament yarn, it is meant that yarn produced by the inventive process. One skilled in the art, once having the benefit of this disclosure, would be able to readily ascertain the annealing roll temperature required to provide finished multifilament yarn having the required tenacity. For instance, the maximum annealing temperature and the relationship between the temperatures of the orientation roll and the annealing roll required to provide finished multifilament yarn having a tenacity of at least 5.6 g/d may vary depending on the composition of the polymer. Preferably, the maximum temperature of the annealing roll will be about 150° C., more preferably less than 149° C., and even more preferably less than 148° C.

The inventive process provides a bio-absorbable and bio-compatible multifilament yarn, having a combination of properties of a) a tensile tenacity of at least 5.6 g/d, b) an elongation of at least about 22%, and c) a strength retention of at least about 50%, as shown by in vivo tests at 6 months in the form of suture or a similar medical device.

Preferred polymers for use in the manufacture of multifilament yarn by processes of the present invention are described in one of U.S. Pat. Nos. 6,045,571, 5,133,739, 4,700,704 or 4,605,730, the contents each of which is hereby incorporated herein in its entirety. Particularly preferred polymers comprising about 95 mole % L-Lactide and about 5 mole % glycolide.

EXAMPLES

In a series of tests, multifilament yarns were produced from a 95/5 mole % L-Lactide/glycolide copolymer according to the conditions set forth in Table 1. As shown therein, orientation temperatures varied from 80° C. to 100° C., while annealing temperatures varied from 138° C. to 148° C. Average tenacity and elongation (n=number of samples) were determined and are set forth in Table 1.

In a comparative example, a 95/5 mole % L-Lactide/glycolide copolymer was extruded and drawn to a draw ratio of 5:1, with the orientation roll set at 98° C. The drawn filaments then were passed to the let-off roll at a constant length (no redrawing, no relaxation) before being wound onto a bobbin. The resulting fiber exhibited a tenacity of 4.8 g/d.

Another comparative example was attempted under conditions similar to the previous example, but the extruded filaments first were drawn to a draw ratio of 6.5:1, (orientation roll set at 98° C.), then relaxed by 2% after annealing. No yarn samples could be produced due to excessive broken filaments.

TABLE 1

Fiber Properties under various orientation and annealing conditions

| Example No. | # of Sample | Roll Speed (fpm) | | | Roll Temperature (° C.) | | Tenacity | Elongation |
|---|---|---|---|---|---|---|---|---|
| | | Orientation | Annealing | Let-Off | Orientation | Annealing | Average (g/d) | Average (%) |
| 1 | 1 | 50 | 275 | 325 | 80 | 138 | 6.5 | 26.0 |
| 2 | 1 | 50 | 275 | 325 | 86 | 136 | 6.2 | 25.1 |
| 3 | 3 | 50 | 275 | 325 | 86 | 143 | 6.4 | 25.8 |
| 4 | 4 | 50 | 275 | 325 | 93 | 138 | 6.0 | 23.8 |
| 5 | 4 | 50 | 275 | 325 | 96 | 138 | 6.2 | 24.0 |
| 6 | 2 | 50 | 275 | 320 | 92 | 148 | 5.5 | 26.3 |
| 7 | 4 | 50 | 275 | 320 | 98 | 138 | 5.3 | 23.2 |
| 8 | 2 | 50 | 275 | 325 | 100 | 140 | 5.4 | 24.4 |

We claim:

1. A process for the manufacture of multifilament yarn, comprising the steps of:

extruding multifilaments of a polymer comprising at least 85 mole percent L-Lactide and not more than 15 mole percent glycolide and spinning said multifilaments to form a spun multifilament yarn, passing said spun multifilament yarn through an orientation roll heated at a temperature of less than 98° C. and drawing said spun multifilament yarn to a draw ratio of at least 4:1 to form an oriented multifilament yarn, annealing said oriented multifilament yarn by passing said oriented multifilament yarn over an annealing roll having a minimum temperature greater than that of the orientation roll and a maximum temperature effective to provide a finished multifilament yarn having a tenacity of at least 5.6 g/d; and redrawing said annealed, oriented multifilament yarn by at least 10 percent at a temperature lower than the temperature of said annealing roll.

2. The process of claim 1 wherein said polymer comprises greater than about 90 mole percent L-Lactide and less than about 10 mole percent glycolide.

3. The process of claim 1 wherein said polymer comprises about 95 mole percent L-Lactide and about 5 mole percent glycolide.

4. The process of claim 3 wherein the temperature of said orientation roll is from about 80° C. to 97° C.

5. The process of claim 4 wherein the temperature of said annealing roll is from about 135° C. to about 145° C.

6. The process of claim 5 wherein the temperature of said orientation roll is about 95° C.

7. The process of claim 6 wherein said redrawing step is conducted at ambient temperature.

8. The process of claim 1 wherein said redrawing step is conducted at ambient temperature.

9. The process of claim 1 wherein said annealed, oriented multifilament yarn is redrawn by from about 10 to about 30 percent.

10. The process of claim 1 wherein said annealed, oriented multifilament yarn is redrawn by from about 15 to about 25 percent.

* * * * *